United States Patent [19]

El Hadary

[11] Patent Number: 5,073,109
[45] Date of Patent: Dec. 17, 1991

[54] FULLY ADJUSTABLE ARTICULATOR DEVICE

[76] Inventor: Khaled A. H. El Hadary, 1066 Gamal Abdel Naser Street, Alexandria, Egypt

[21] Appl. No.: 649,508

[22] Filed: Feb. 4, 1991

[30] Foreign Application Priority Data

Feb. 4, 1990 [EG] Egypt ................................ 52/90

[51] Int. Cl.⁵ .............................................. A61C 11/00
[52] U.S. Cl. ...................................... 433/57; 433/61; 433/63
[58] Field of Search ...................... 433/57, 61, 62, 63, 433/65, 68, 69

[56] References Cited

U.S. PATENT DOCUMENTS

| | | | |
|---|---|---|---|
| 1,586,739 | 6/1926 | Hanau | 433/57 |
| 2,549,339 | 4/1951 | Shore | 433/57 |
| 2,909,837 | 10/1959 | Gerber | 433/57 |
| 3,159,915 | 12/1964 | Beu et al. | 433/57 |
| 4,968,256 | 11/1990 | Lang et al. | 433/57 |

*Primary Examiner*—John J. Wilson
*Attorney, Agent, or Firm*—Thomas R. Vigil

[57] ABSTRACT

An articulator device for establishing the articulated movement of a mandible of a jaw relative to a maxilla of a jaw comprising a lower part, an upper part positioned above the lower part and having two spaced apart condylar houses each including an outer vertical frame, a middle horizontal frame and an inner vertical frame, each for mounting a sheet or plate having a curvalinear edge surface representing movement of a mandible, and first and second condylar rods each adjustably mounted to the lower part and having an upper vertical rod portion and an upper horizontal rod portion.

3 Claims, 5 Drawing Sheets

FULLY ADJUSTABLE ARTICULATOR DEVICE

BACKGROUND OF THE INVENTION

1. Field of the Invention

The present invention relates to an articulator device for simulating the three dimensional articulated movement of a mandible of a jaw relative to a maxilla of a jaw.

2. Description of the related art including information disclosed under 37 CFR §§ 1.97-1.99

Heretofore various articulator devices for imitating the three dimensional movement of the mandible of a jaw have been proposed.

The articulator device of the present invention differs from the previously proposed articulator devices by providing an easily operable and simply constructed device by which adjustment of the condylar rods and condylar houses of the articulator device are simply and easily effected and wherein movement of each condylar rod is guided in only two pathways, one vertical and the other horizontal, but in such a way that the combined vertical and horizontal movement results in a three dimensional condyle movement.

SUMMARY OF THE INVENTION

According to the invention there is provided an articulator device for establishing the articulated movement of a mandible of a jaw relative to a maxilla of a jaw comprising a lower part, an upper part positioned above the lower part and having two spaced apart condylar houses each including an outer vertical frame, a middle horizontal frame and an inner vertical frame, each for mounting a sheet or plate having a curvalinear edge surface representing movement of a mandible, and first and second condylar rods each adjustably mounted to the lower part and having an upper vertical rod portion and an upper horizontal rod portion.

BRIEF DESCRIPTION OF THE PREFERRED EMBODIMENT(S)

Figure 1:
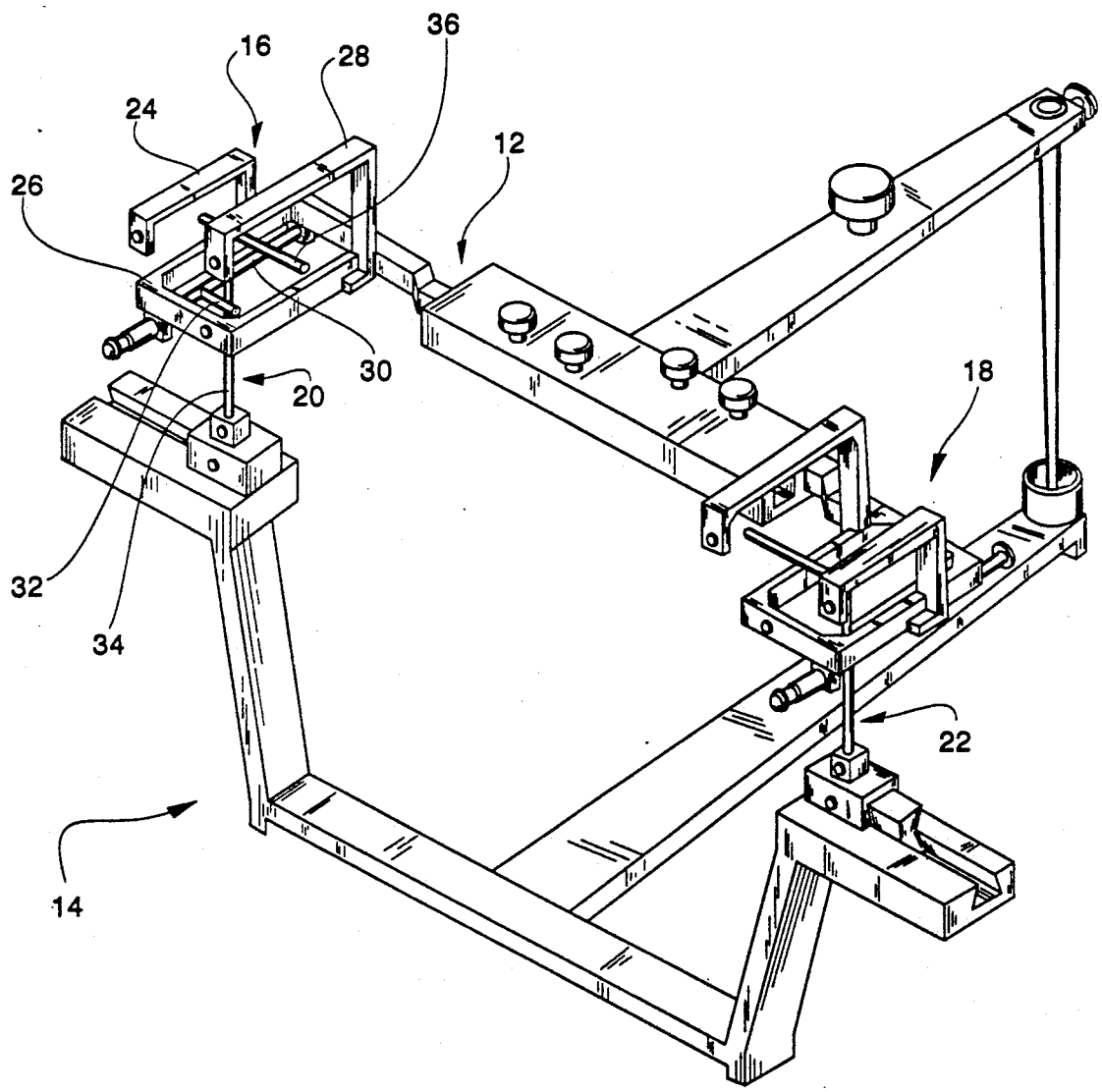
FIG. 1 is a perspective view of the articulator device of the present invention.

The articulator device 10 is a mechanical device 10 and is used in the dental field to simulate all the mandibular movements performed by a patient.

The device 10 comprises two main parts 12 and 14, the upper part 12 resembling the upper jaw (maxilla) and the lower part 14 resembling the lower jaw (mandible). The upper part 12 contains two condylar houses 16 and 18. The distance between the two condylar houses 16, 18 is adjusted to be equal to the same distance between two lower condylar rods 20 and 22.

Each condylar house comprises three frames (outer vertical frame 24, middle horizontal frame 26 and inner vertical frame 28) connected to each other in a specific way. These frames are adapted to carry three sheets such as plastic sheets. The middle horizontal frame 26 comprises a long rod 30 rotatable into and guide fixed at the lower border in the anterior and posterior side of the middle horizontal frame 26, and another short rod 32 extending from the longer rod 30 and perpendicular to it, and this short rod may be in front of or behind the condylar rod 20 of the lower part 14 of the articulator device 10.

Each condylar rod 20, 22 has a specific design. It comprises two rod portions 34 and 36. The first rod portion 34 is a vertical rod portion 34 and the second rod portion 36 is a horizontal rod portion 36. There is a definite relation between the two rod portions 34, 36 which determines how the two rod portions 34, 36 will be arranged. This relation is the relation between the tips 41, 42 (FIG. 2) of a drawing stylus of a pantograph.

Figure 2:
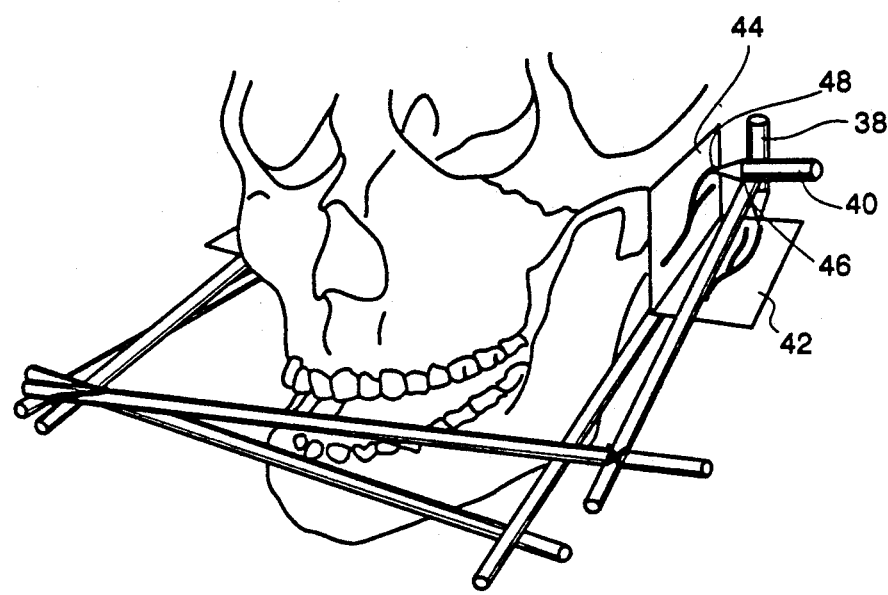
FIG. 2 is a perspective view of a pantograph stylus associated with a mandible or lower jaw forming part of and coupled to a skull, a portion of which is shown in FIG. 2.
Figure 2A:
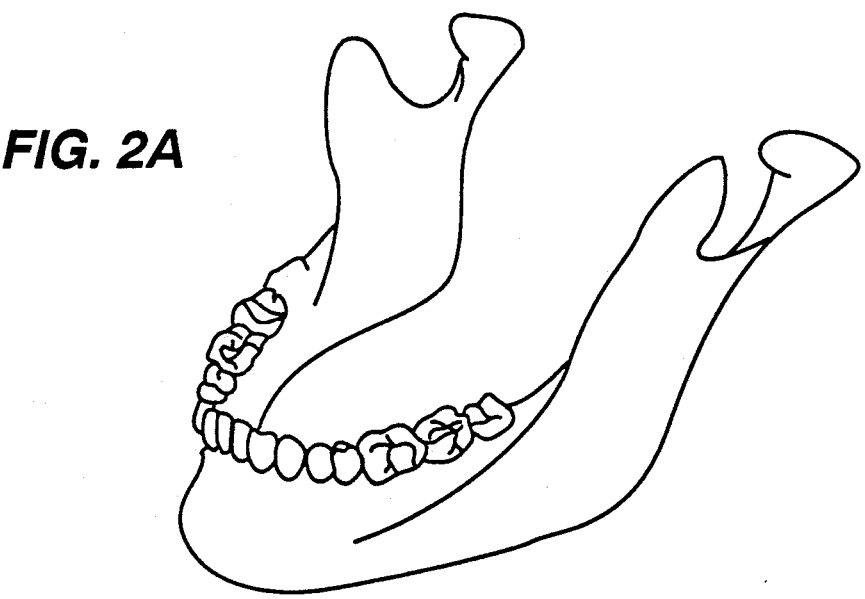
FIG. 2A is a perspective view of a mandible.

In FIG. 2 there is shown that (1) a vertical drawing stylus 38 is behind a horizontal stylus 40, (2) the vertical stylus 38 draws the movement on a horizontal record table 42, (3) the horizontal stylus 40 draws the movement on a vertical record table 44, and (4) the ordinates of the tips' points 46, 48, of each stylus 38, 40 are different in the X, Y, Z axis.

Figure 3:
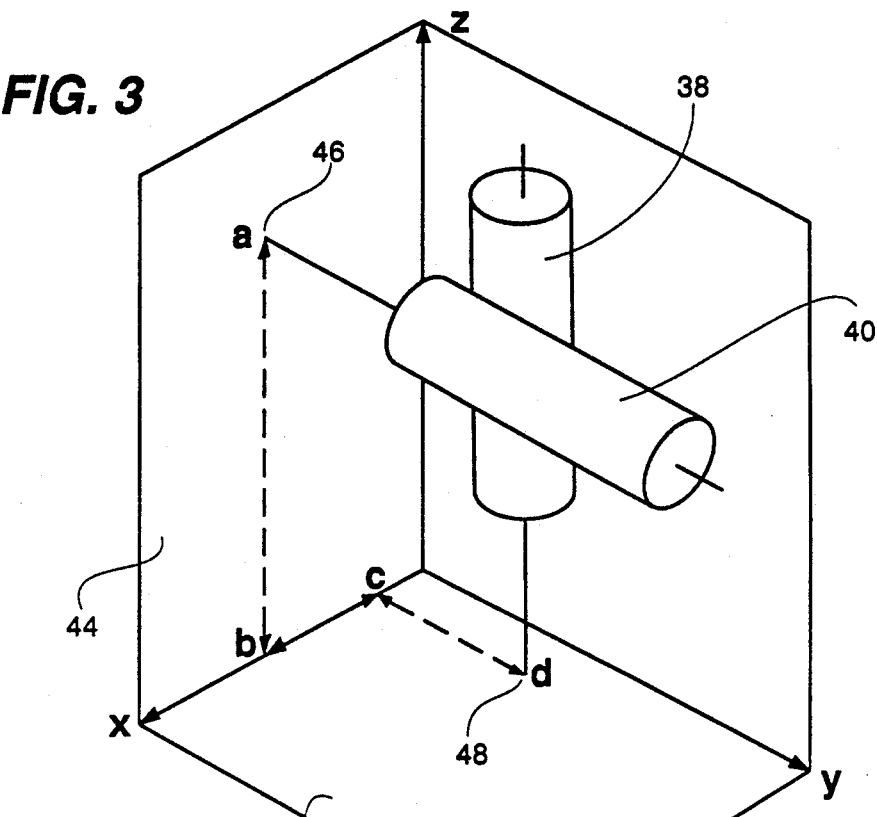
FIG. 3 is a perspective view of a vertical stylus and a horizontal stylus and the three dimensional relationship between the center lines of each stylus.
Figure 4:
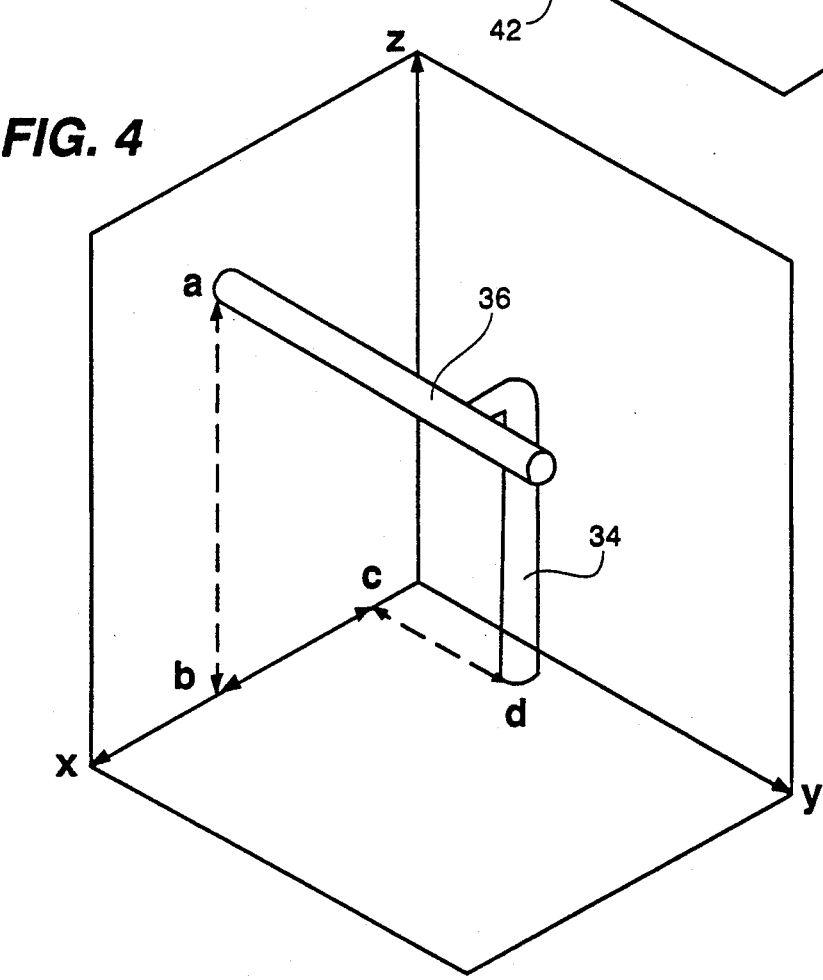
FIG. 4 is a perspective view of the rod portions of one of the condylar rods of the articulator device and shows how the three dimensional relationship of the rod portions corresponds to the three dimensional relationship of the axes of the two styluses shown in FIG. 3.

In FIG. 3 the tip 46 of the vertical stylus 38 is lower than the tip 48 of the horizontal stylus 40 by the distance a.b, and behind it by the distance b.c and outer to it by the distance c.d. In the arrangement of the parts of the condylar rod 20 or 22, these different distances a.b, b.c and c.d must be the same for the inner end of the horizontal rod portion 36 and the side of the vertical rod portion 34 as shown in FIG. 4.

Figure 5:
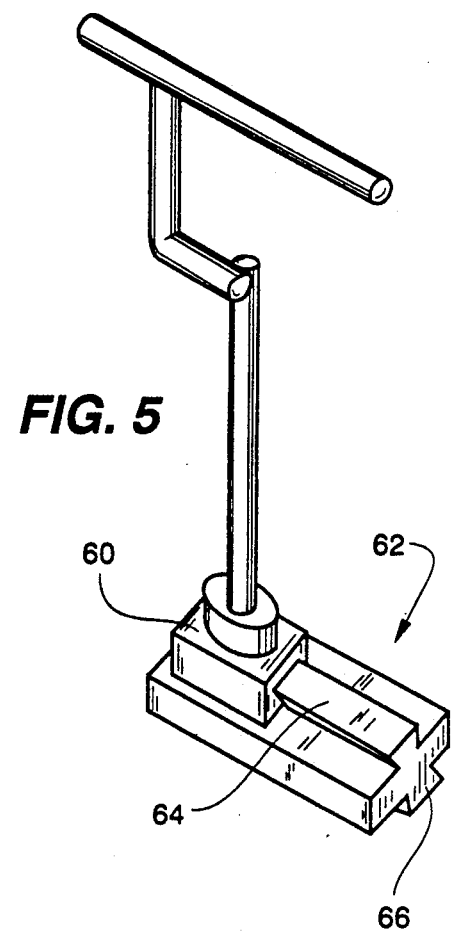
FIG. 5 is a perspective view of the mounting of the base of one of the condylar rods in a dove tail manner on a track of a lower part of the articulator device.
Figure 7:
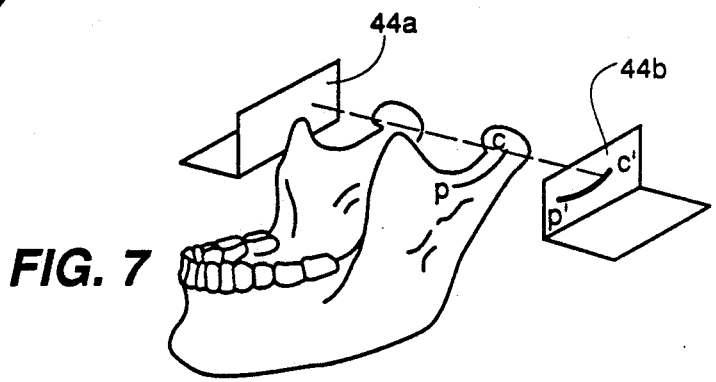
FIG. 7 is a perspective view of the mandible, the horizontal sheets and the vertical sheets shown in FIG. 6.

The distance between the two condylar rods 20, 22 is adjusted to be equal to the distance between the two vertical record tables 44a, 44b (FIG. 7) of the pantograph. This adjustment is done by moving a base 60 of the condylar rod 20 or 22 (FIG. 5) on a double dove tail track 62 (FIG. 5) together as one piece. The condylar rods 20, 22 have another adjustment. Their bases 60 can move on an upper track 64, or the lower track 66 of the double dove tail track 62 can be moved on a mating track inward or outward.

Figure 10:
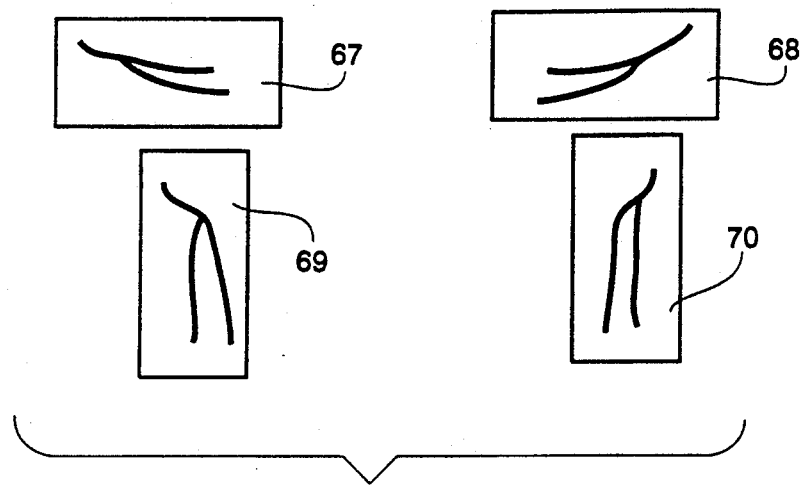
FIG. 10 are plan views of four pantograph drawing records representing condylar movement in three dimensions.
Figure 11:
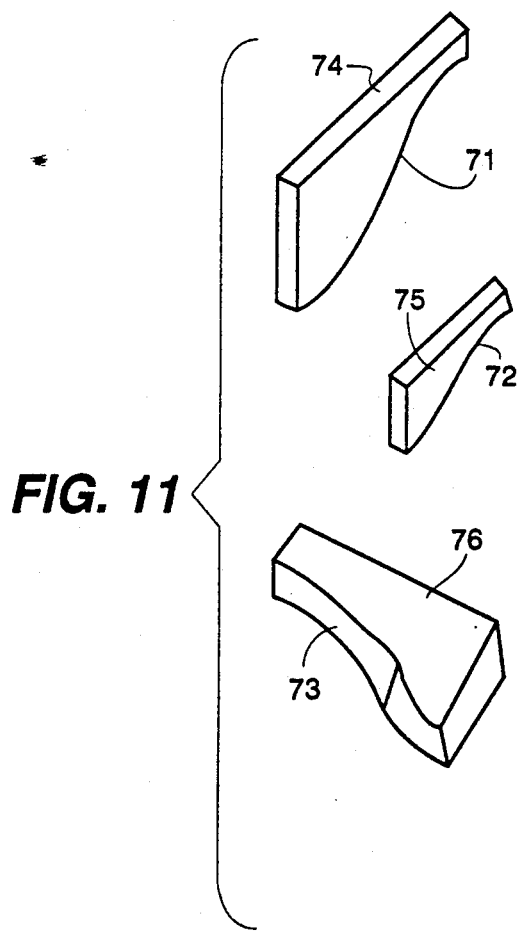
FIG. 11 is an array of three sheets or plates each having a curvalinear surface on one edge thereof which is developed from one of the drawings records shown in FIG. 10.

The pantographic drawing records 67, 68, 69 and 70 (FIG. 10) represent the condylar movement in three dimension developed by making drawings in two perpendicular planes. And in the articulator device 10, to simulate this movement two pathways are developed on edge surfaces 71, 72 and 73 of three plates 74, 75 and 76 shown in FIG. 11 (as it is recorded by the pantograph) for the condylar rod 20 or 22, so the resulting movements will be in three dimensions.

On the posterior record tables 42a, 42b, 44a, 44b of the pantograph at the level of the condyle, there are two drawing records for each condyle (the left and the right). One drawing is recorded on the vertical table 44a, 44b and the other on the horizontal table 42a, 42b.

Figure 6:
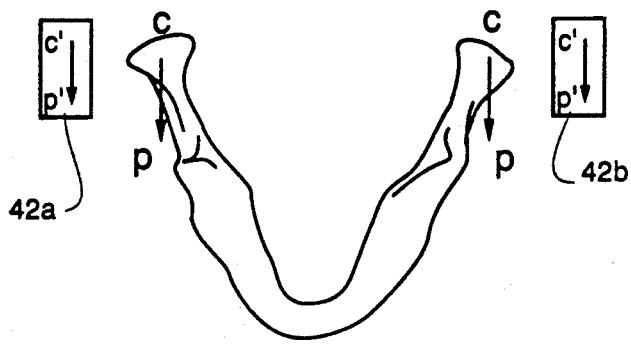
FIG. 6 is a top plan view of the mandible and the horizontal sheets on which each vertical stylus moves and shows protrusive excursion of the mandible.

There is a centric point (C) from which the condyle starts any movement. The movements of the condyles can be:

(I) In the protrusive excursion of the mandible the two condyles move together with movement forward and downward. This movement in a horizontal path (FIG. 6) is represented as two straight lines c.p and the stylus simultaneously scribe path c'.p' on the horizontal tables 42a, 42b. In the vertical path (FIG. 7), this movement is represented as a curve going forward and downward starting from the (C) point on the vertical tables 44a, 44b.

(II) In the lateral movement (if the mandible moves to the right side) the left condyle (orbiting condyle) will go forward and inward and downward, and orbit around the right condyle (rotating condyle) which simultaneously rotates and moves outward, upward and backward.

Figure 8:
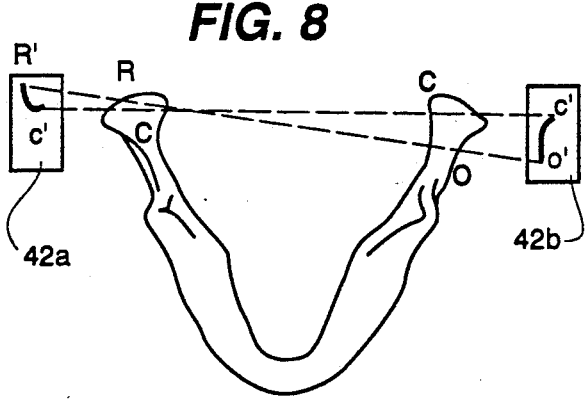
FIG. 8 is a top plan view of the mandible and the horizontal sheets on which each vertical stylus moves and shows lateral movement of the mandible.
Figure 9:
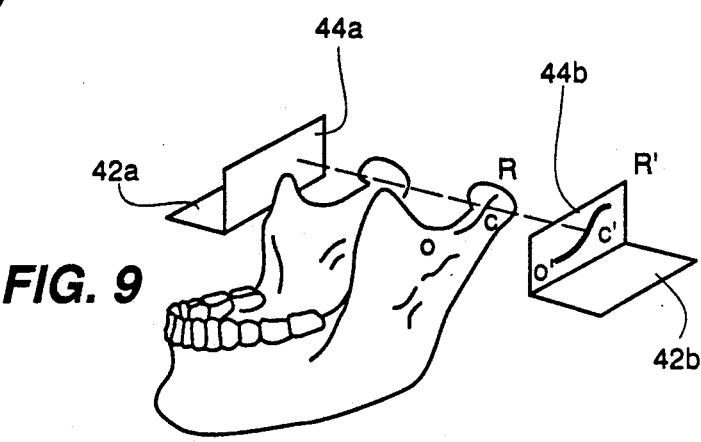
FIG. 9 is a perspective view of the mandible, the horizontal sheets and the vertical sheets shown in FIG. 8.

(III) In the horizontal plane, the movement of the orbiting condyle (left one) is represented as an orbiting condylar in the C.O path (FIG. 8). In the vertical plane, the movement of the orbiting condyle (left condyle) is represented as an orbiting condylar path C'.O' on the left vertical record table 44a (FIG. 9), and the rotating condyle (the right one) moves in C.R path, as C'R' on the right vertical record table 44b.

The record blanks are removed from the pantograph (the blanks should be identified according to their position on the pantograph) and put on suitable plastic plates or sheets. Then the plastic sheet or plate is cut by following the curves on the drawings.

From the vertical record blanks a protrusive path is developed on the sheets or plates 74 and 75 (FIG. 11) and these plastic sheets 74, 75 are used for the protrusive path and the sheets or plates 74, 75 are cut accordingly.

After this step, three plastic sheets or plates 74, 75 76 for each condyle having curvalinear edges 71, 72, 73 representing the movement of the condyle on the record tables of the pantograph are obtained.

Then the two parts of the articulator device 10 are separated and the distance between the condylar houses 16, 18 of the upper part 12, and between the condylar rods 20, 22 of the lower part 14 are adjusted to be equal to the same distance between the two vertical record tables 44a, 44b of the pantograph.

Then each plastic sheet 74, 75, 76 is placed in the suitable frame in the condylar house 16 or 18.

The sheet 74 of the protrusive movement is placed in the outer vertical frame 24.

The sheet 75 of the orbiting and rotating movement in the vertical plane is placed in the inner vertical frame 28.

The sheet 76 of the orbiting and rotating movement in the horizontal plane is placed in the middle horizontal frame 26.

All the plastic sheets on both sides must be accurately secured in their places.

The bases of the condylar rods 20, 22 are adjusted to move in an inward direction on the double dove tail track 62.

The upper part of the articulator device 10 is replaced to the lower part and the condylar rod control directed downward after the horizontal rod is firmly rested under the inner edge of the inner vertical sheet, and the side of the vertical rod is attached to the lateral edge of the horizontal sheet.

The condylar rod control is then adjusted to place it behind the condylar rod. In this position, the condylar rods 20, 22 are in the centric position.

If it is desired to simulate the right lateral movement, the condylar rod control is changed to be in front of the right condylar rod 22 and the left one to be behind the left condylar rod 20.

If it is desired to simulate the left lateral movement, the left control is positioned to be in front of the left condylar rod 20, and the right control to be behind the right condylar rod 22.

In protrusive movement, the two condylar rod controls are adjusted to be behind the two condylar rods 20, 22 and the bases 60 of the condylar rods 20, 22 are slid to outward on the double dove tail track 62. Now the horizontal part or rod portions 36 of the condylar rods 20, 22 will be under the lower edge of the protrusive plastic sheets.

The articulator device 10 of the present invention comprising the condylar rods 20 and 22 each having a vertical rod portion 34 and a horizontal rod portion 36 provide for guided movement in two pathways at the same time, one pathway being in a vertical plane and the other pathway being in a horizontal plane such that the combined movement in the two planes results in a three dimensional condyle movement. Other advantages are described below.

The paths of movement on side edges 71-73 are developed from only four drawing records from the pantograph.

The mechanical adjustment for the condylar houses 16 and 18 is a single adjustment of the width between the two condylar houses 16 and 18; and a simple double dove tail track is provided for condylar rod control.

Two different pathways are provided for both the protrusive, the lateral and the orbiting movements of the inner ends of the mandible which are separated from each other.

I claim:

1. An articulator device for establishing the articulated movement of a mandible of a jaw relative to a maxilla of a jaw comprising a lower part, an upper part positioned above the lower part and having two spaced apart condylar houses each including an outer vertical frame, a middle horizontal frame and an inner vertical frame, each for mounting a sheet or plate having a curvalinear edge surface representing movement of a mandible, and first and second condylar rods each adjustably mounted to the lower part and having an upper vertical rod portion and an upper horizontal rod portion.

2. The articulator device of claim 1 wherein said vertical rod portion and said horizontal rod portion have a specific relationship identical to the relationship of a vertical drawing stylus located behind a horizontal drawing stylus.

3. The articulator device of claim 1 wherein each condylar rod has a base mounted on a double dove tail track.

* * * * *